United States Patent
Cho et al.

(10) Patent No.: US 8,116,851 B2
(45) Date of Patent: Feb. 14, 2012

(54) LIVING BODY MEASUREMENT APPARATUS WITH WAVEGUIDE LIGHT SOURCE AND LIGHT EXTRACTING PATTERN

(75) Inventors: Jae-Geol Cho, Yongin-si (KR); Kyoung-Youm Kim, Seoul (KR); In-Duk Hwang, Suwon-si (KR); Kun-Kook Park, Suwon-si (KR)

(73) Assignee: Samsung Electronics Co., Ltd., Yeongtong-Gu, Suwon-Si, Gyeonggi-Do (KR)

( * ) Notice: Subject to any disclaimer, the term of this patent is extended or adjusted under 35 U.S.C. 154(b) by 992 days.

(21) Appl. No.: 11/787,964

(22) Filed: Apr. 18, 2007

(65) Prior Publication Data
US 2008/0039729 A1 Feb. 14, 2008

(30) Foreign Application Priority Data
Aug. 10, 2006 (KR) .................. 10-2006-0075764

(51) Int. Cl.
*A61B 6/00* (2006.01)
(52) U.S. Cl. .................. 600/473; 600/476; 600/310
(58) Field of Classification Search .................. 600/473, 600/476, 310, 475, 477; 382/124, 115; 250/341.8
See application file for complete search history.

(56) References Cited

U.S. PATENT DOCUMENTS

| | | | |
|---|---|---|---|
| 4,633,087 A | 12/1986 | Rosenthal et al. | 250/341 |
| 4,850,365 A | 7/1989 | Rosenthal | 128/664 |
| 4,928,014 A | 5/1990 | Rosenthal | 250/341 |
| 5,014,713 A | 5/1991 | Roper et al. | 128/664 |
| 5,285,783 A * | 2/1994 | Secker | 600/323 |
| 5,419,321 A | 5/1995 | Evans | 128/633 |
| 5,820,558 A | 10/1998 | Chance | 600/473 |
| 6,134,458 A | 10/2000 | Rosenthal | 600/310 |
| 6,285,904 B1 | 9/2001 | Weber et al. | 600/473 |
| 2002/0084417 A1* | 7/2002 | Khalil et al. | 250/341.8 |
| 2002/0183624 A1 | 12/2002 | Rowe et al. | |
| 2004/0179722 A1 | 9/2004 | Moritoki et al. | |

(Continued)

FOREIGN PATENT DOCUMENTS

| | | |
|---|---|---|
| CN | 1124109 | 10/2003 |
| CN | 1700882 | 11/2005 |
| EP | 0286142 A2 | 10/1988 |
| EP | 0 516 251 | 12/1992 |

(Continued)

OTHER PUBLICATIONS

Webster, J. G.; "Design of Pulse Oximeters;" IOP Publishing Ltd., UK; 1997.

*Primary Examiner* — Brian Casler
*Assistant Examiner* — Rajeev Siripurapu
(74) *Attorney, Agent, or Firm* — Cha & Reiter, LLC

(57) ABSTRACT

Disclosed is a living body measurement apparatus including: a first light source placed on the surface of the skin in a living body and radiating a first light in a visible light wavelength range onto the surface of the skin; a second light source placed on the surface of the skin and radiating a second light in a near-infrared wavelength range onto the surface of the skin; an optical detector placed on the surface of the skin at a predetermined distance from the first and second light sources to detect, as an electric signal, first or second detection light penetrating up through the skin and inputted thereto among the radiated first or second light; and a controller for sequentially driving the first and second light sources.

16 Claims, 17 Drawing Sheets

U.S. PATENT DOCUMENTS

| | | | |
|---|---|---|---|
| 2005/0055244 A1* | 3/2005 | Mullan et al. | 705/2 |
| 2005/0058456 A1* | 3/2005 | Yoo | 398/140 |
| 2005/0265586 A1 | 12/2005 | Rowe et al. | |
| 2005/0288591 A1* | 12/2005 | Kondoh et al. | 600/473 |
| 2006/0041198 A1* | 2/2006 | Kondoh et al. | 600/473 |

FOREIGN PATENT DOCUMENTS

| | | |
|---|---|---|
| EP | 0942260 A1 | 9/1999 |
| EP | 1 013 219 | 6/2000 |
| JP | 10-094523 | 4/1998 |
| KR | 2007-0092869 | 9/2007 |

\* cited by examiner

LIVING BODY MEASUREMENT APPARATUS WITH WAVEGUIDE LIGHT SOURCE AND LIGHT EXTRACTING PATTERN

CLAIM OF PRIORITY

This application claims priority to an application entitled "Living Body Measurement Apparatus" filed with the Korean Intellectual Property Office on Aug. 10, 2006 and assigned Serial No. 2006-75764, the content of which is hereby incorporated by reference.

BACKGROUND OF THE INVENTION

1. Field of the Invention

The present invention relates to an apparatus and a method for measuring a living body, and more particularly, to an apparatus and a method for measuring living body composition, such as skin and subcutaneous fat, using light.

2. Description of the Related Art

A number of different methods for measuring body fat percentage or subcutaneous fat thickness are known. For example, methods using calipers, ultrasound, computer tomography (CT), magnetic resonance imaging (MRI) are some of the known methods for measuring subcutaneous fat thickness. However, measurement with calipers often may be inaccurate, inconvenient, and cause pain to a person receiving the measurement. Other measurement methods involving use of ultrasound, CT, or MRI require use of expensive medical imaging machines that are operated by professionals who are trained to use the machines. In addition, such measurement machines are not portable, and cannot be used readily at a desired place or time. As a solution to these problems, various living body measurement methods using light have been proposed.

According to the proposed methods using light, body fat percentage or subcutaneous fat thickness is measured by radiating light onto the surface of the skin and detecting the light emitted from the surface of the skin by multiple scattering. Such measurement is non-invasive, and takes a short time. Since a small portable apparatus is generally designed for that measurement, it can be used wherever and whenever necessary.

FIG. 1 is a view illustrating a conventional apparatus for measuring subcutaneous fat thickness. A living body tissue 130 has a structure made up of muscle 132, fat 134 and skin 136 with thickness ranging from 0.5 to 4 mm. The skin 136 is divided into stratum corneum, epidermis and dermis. The apparatus 100 for measuring subcutaneous fat thickness includes a light emitting diode ("LED") 110 and a photodiode ("PD") 120. The LED 110 and the PD 120 are separated from each other and placed on the top surface of the skin 136. The LED 110 emits light in near-infrared bandwidth onto the surface of the skin 136. A portion of the light traveling from the surface of the skin 136 to the muscle 132 is reflected back to the skin 136 by multiple scattering, while rest is absorbed by the muscle 132. The PD 120 detects the light emitted from the surface of the skin 136 as an electric signal, after converting the emitted light to an electrical signal.

FIG. 2 is a graph showing output variations of the PD 120 according to the distance from the LED 110. The transverse axis of the graph represents the thickness, in mm, of the subcutaneous fat 134, whereas the longitudinal axis represents the output voltage V of the PD 120. The term "SD" refers to the distance between the LED 110 and the PD 120. FIG. 2 depicts points plotted on curves that map subcutaneous fat thickness to the corresponding output voltage in SDs of 5 mm, 10 mm, and 20 mm. The graph in FIG. 2 shows that the output of the PD 120 gradually increases with an increase of the thickness of the subcutaneous fat 134, but does not increase further from a specific thickness level. From this graph, it is clear that greater the distance SD, broader range of subcutaneous fat thickness may be measured.

U.S. Pat. No. 4,850,365 titled "Near Infrared Apparatus and Method for Determining Percent Fat in a Body" and issued to Rosenthal et al. discloses a method and an apparatus for measuring body fat percentage by transmitting near-infrared radiation at only one wavelength into the skin and detecting the light emitted from the surface of the skin due to multiple scattering within the subcutaneous fat.

U.S. Pat. No. 4,633,087 titled "Near Infrared Apparatus for Measurement of Organic Constituents of Material" and issued to Rosenthal et al. discloses a technique for measuring body fat percentage by transmitting near-infrared radiation of different wavelengths into the skin and detecting the light emitted from the surface of the skin due to multiple scattering within the subcutaneous fat.

The conventional methods of measuring body fat or subcutaneous fat, however, have several shortcomings. In particular, the output of the PD is affected by the skin thickness and color, as well as the thickness of the subcutaneous fat. The conventional methods, however, cannot and do not effectively compensate any errors attributable to the thickness and the color of the skin.

SUMMARY OF THE INVENTION

The present invention has been made to solve the above-mentioned problems occurring in the prior art and provides additional advantages. The present invention provides a living body measurement apparatus for determining skin thickness and color, and accurately measuring subcutaneous fat thickness based on the determined thickness and color of the skin.

In accordance with one aspect of the present invention, there is provided a living body measurement apparatus including: a first light source placed on the surface of the skin in a living body and radiating a first light in a visible light wavelength range onto the surface of the skin; a second light source placed on the surface of the skin and radiating a second light in a near-infrared wavelength range onto the surface of the skin; an optical detector placed on the surface of the skin at a predetermined distance from the first and second light sources to detect, as an electric signal, first or second detection light penetrating up through the skin and inputted thereto among the radiated first or second light; and a controller for sequentially driving the first and second light sources.

In accordance with another aspect of the present invention, there is provided a living body measurement apparatus including: a first light source placed on the surface of the skin in a living body and radiating a first light having a first wavelength onto the surface of the skin; a second light source placed on the surface of the skin and radiating a second light having a second wavelength which is different from the first wavelength onto the surface of the skin; a third light source placed on the surface of the skin at a location more remote from an optical detector than the first and second light sources, and radiating a third light onto the surface of the skin; an optical detector for detecting, as an electric signal, first, second or third detection light penetrating up through the skin and inputted thereto among the radiated first, second or third light; and a controller for sequentially driving the first, second and third light sources.

BRIEF DESCRIPTION OF THE DRAWINGS

The above features and advantages of the present invention will be more apparent from the following detailed description taken in conjunction with the accompanying drawings, in which.

DETAILED DESCRIPTION OF THE INVENTION

Hereinafter, several aspects of the present invention will be described with reference to the accompanying drawings. For purpose of simplicity and clarity, detailed descriptions of known and/or repetitive components, functions, and configurations are omitted, as they may make the subject matter of the present invention unclear.

Figure 1:
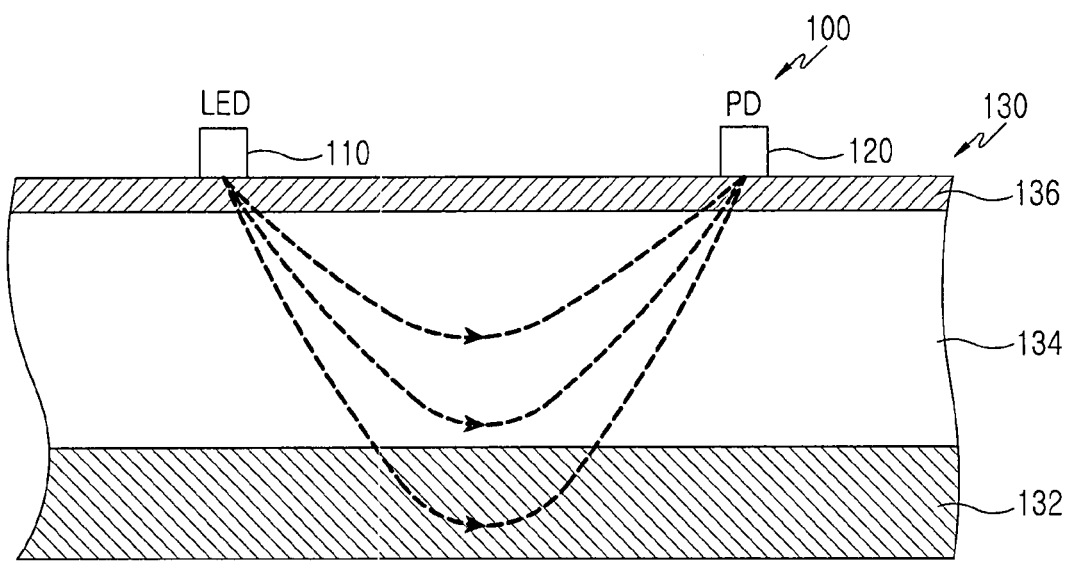
FIG. 1 is a view illustrating a conventional apparatus for measuring subcutaneous fat thickness in the prior art.
Figure 2:
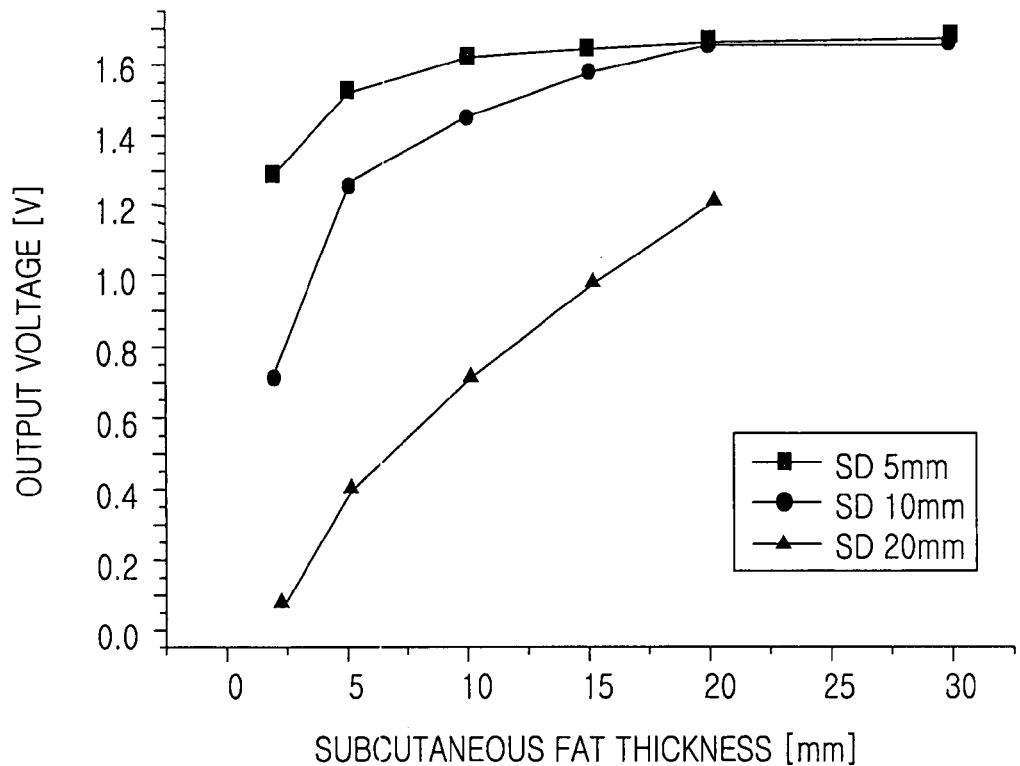
FIG. 2 is a graph showing output variations of a photodiode according to the subcutaneous fat thickness and the distance from a light emitting diode.
Figure 3:
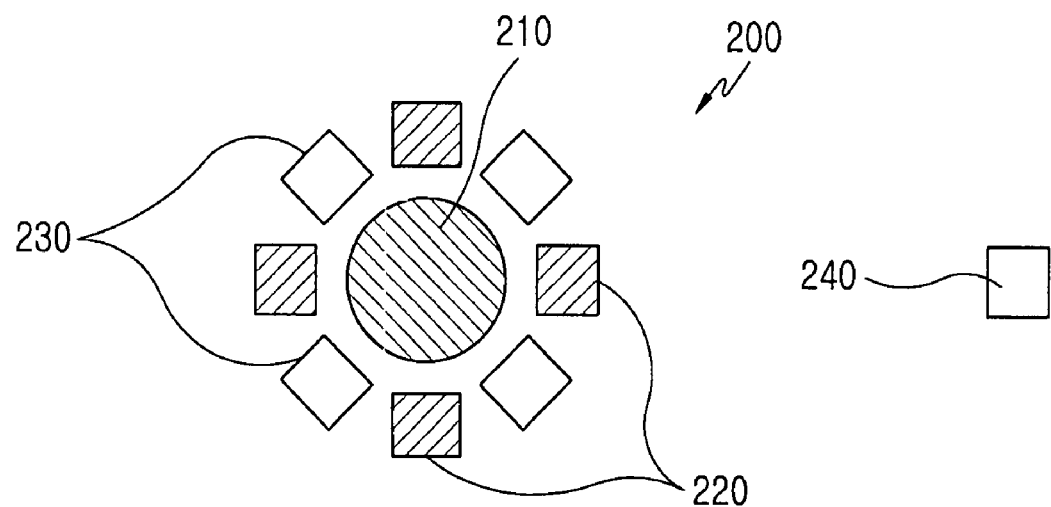
FIG. 3 illustrates a living body measurement apparatus according to a first aspect of the present invention.
Figure 4:
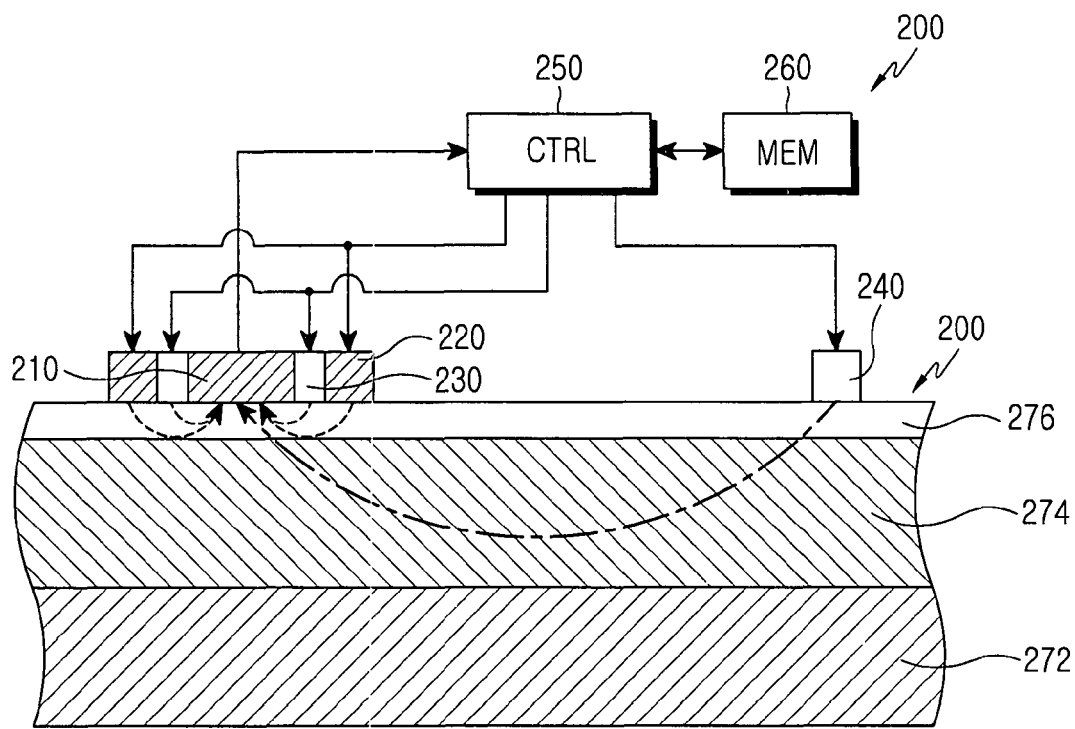
FIG. 4 is a cross-sectional view of the living body measurement apparatus in FIG. 3.

FIG. 3 illustrates a living body measurement apparatus according to a first aspect of the present invention. FIG. 4 is a cross-sectional view of the living body measurement apparatus in FIG. 3. A living body tissue 270 has a structure made up of muscle 272, fat 274 and skin 276. A living body measurement apparatus 200 includes an optical detector 210, a plurality of first light sources 220, a plurality of second light sources 230, a third light source 240, a controller 250 and a memory 260. The controller 250 and the memory 260 are not depicted in FIG. 3.

The optical detector 210 is placed on top of the skin 276 and outputs an electric signal obtained by photoelectric conversion of the inputted light. In other words, the optical detector 210 detects the light penetrating up through the skin 276 and inputted thereto as an electric signal, after converting the inputted light into an electrical signal. The bottom of the optical detector 210, which functions as an input terminal, may be in a direct contact with the surface of the skin 276, or, alternatively, be separated from the surface of the skin 276. A typical photodiode can be used as the optical detector 210.

The plurality of first light sources 220 (four depicted in FIG. 3) and the plurality of second light sources 230 (four depicted in FIG. 3) are disposed at an equal distance from and along the outer perimeter of the optical detector 210. The first and second light sources 220 and 230 are reciprocally disposed, and each of the light sources 220 and 230 are equally spaced from adjacent light sources.

The first light sources 220 are disposed on the surface of the skin 276 at a predetermined distance from the optical detector 210. The first light sources 220 radiate a first light having a first wavelength, for example, 660 nm, in a visible light bandwidth onto the surface of the skin 276 (the first light is indicated by a solid line in FIG. 4). The bottom of each first light source 220, which functions as an output terminal, may be in a direct contact with the surface of the skin 276, or, alternatively, separated from the surface of the skin 276. Typical light emitting diodes ("LEDs") or laser diodes ("LDs") can be used as the first light sources 220.

The second light sources 230 are disposed on the surface of the skin 276 at a certain distance from the optical detector 210. The second light sources 230 radiate a second light having a second wavelength, for example, 940 nm, in a near-infrared bandwidth onto the surface of the skin 276 (the second light is indicated by a dotted line in FIG. 4). The bottom of each second light source 230, which functions as an output terminal, may be in a direct contact with the surface of the skin 276, or, alternatively, separated from the surface of the skin 276. Typical LEDs or LDs can be used as the second light sources 230.

The third light source 240 is disposed on the surface of the skin 276 at a greater distance from the optical detector 210 than the first and second light sources 220 and 230. The third light source 240 radiates a third light having a wavelength in a near-infrared bandwidth onto the surface of the skin 276 (the third light is indicated by an one-dot chain line in FIG. 4). For example, the third light source 240 may radiate the wavelength of 940 nm. The bottom of the third light source 240, which functions as an output terminal, may be in a direct contact with the surface of the skin 276, or, alternatively, separated from the surface of the skin 276. A typical LED or LD can be used as the third light source 240.

Although the optical detector 210, first light sources 220, second light sources 230 and third light source 240 may be separated slightly from the surface of the skin during measurement of body composition, the separation will reduce the optical coupling efficiency and the measurement accuracy attributable to an alignment error.

In accordance with the first aspect of the present invention, the first and second light sources 220 and 230 may be separated from the optical detector 210 at a distance of not more than 5 mm, and the third light source 240 may be separated from the optical detector 210 at a distance of not less than 10 mm. Preferably, the distance between the optical detector 210 and each of the first and second light sources 220 and 230 is 2 mm, and the distance between the optical detector 210 and the third light source 240 is 10 mm. Such configurations of the light sources 220 and the optical detector 210 enables the first aspect of the present invention to measure the thickness of the subcutaneous fat with much accuracy.

In particular, the first and second light sources 220 and 230 are used to measure the skin 276. As such, to minimize any influence the thickness of the subcutaneous fat 274 may have on the measurement of the skin 276, it is preferable to separate each of the first and second light sources 220 and 230 from the optical detector 210 at a distance of not more than 5 mm.

The third light source 240, meanwhile, is used to measure the subcutaneous fat 274. To measure a broad range of the thickness of the subcutaneous fat, it is preferable to separate the third light source 240 from the optical detector 210 at a distance of not less than 10 mm.

Further, as collagen fibers contained in the skin 276 have asymmetric optical directional characteristics, disposition of the plurality of first light sources 220 at equal intervals around the outer periphery of the optical detector 210 enables the first aspect of the present invention to compensate the directional characteristic of the skin 276. The plurality of second light sources 230 are used in the first aspect of the present invention for the same reason.

Although a plurality of the first light sources 220 and a plurality of the second light sources 230 are used in the first aspect of the present invention, a person of ordinary skill in the art will appreciate that it is also possible to use a single first light source 220 and/or a single second light source 230.

Hereinafter, light inputted to the optical detector 210 among the rays of the first light radiated from the first light sources 220 will be referred to as "first detection light." Light inputted to the optical detector 210 among the rays of the second light radiated from the second light sources 230 will be referred to as "second detection light." Also, light inputted to the optical detector 210 among the rays of the third light radiated from the third light source 240 will be referred to as "third detection light."

The memory 260 stores a first table showing two relationships. First, the first table shows the relationship between the intensities of the first and second detection lights and the thickness of the skin 276. In addition, the first table shows the relationship between the intensities of the first and second detection lights and the color of the skin 276. The memory 260 also stores a second table showing the relationship between the thickness of the subcutaneous fat 274 and the intensity of the third detection light according to the thickness and color of the skin 276.

For purpose of explaining the present invention, the intensity of light may be represented by an output voltage of the optical detector 210. The color of the skin 276, meanwhile, may be represented by melanin index. For purpose of convenience, white, yellow, and black skin colors will be quantified using standard melanin indexes. For example, the skin of white color or lighter color may be represented as the skin with low melanin index; the skin of yellow color or intermediate color may be represented as the skin with intermediate melanin index; and the skin of black color or darker color may be represented as the skin with high melanin index. Also, for purposes of convenience and brevity, a detailed description of the characteristics of the skin with intermediate melanin index, the "yellow" skin may be omitted when unnecessary, as such skin has the characteristics between the skin with high melanin index and the skin with low melanin index.

Figure 5:
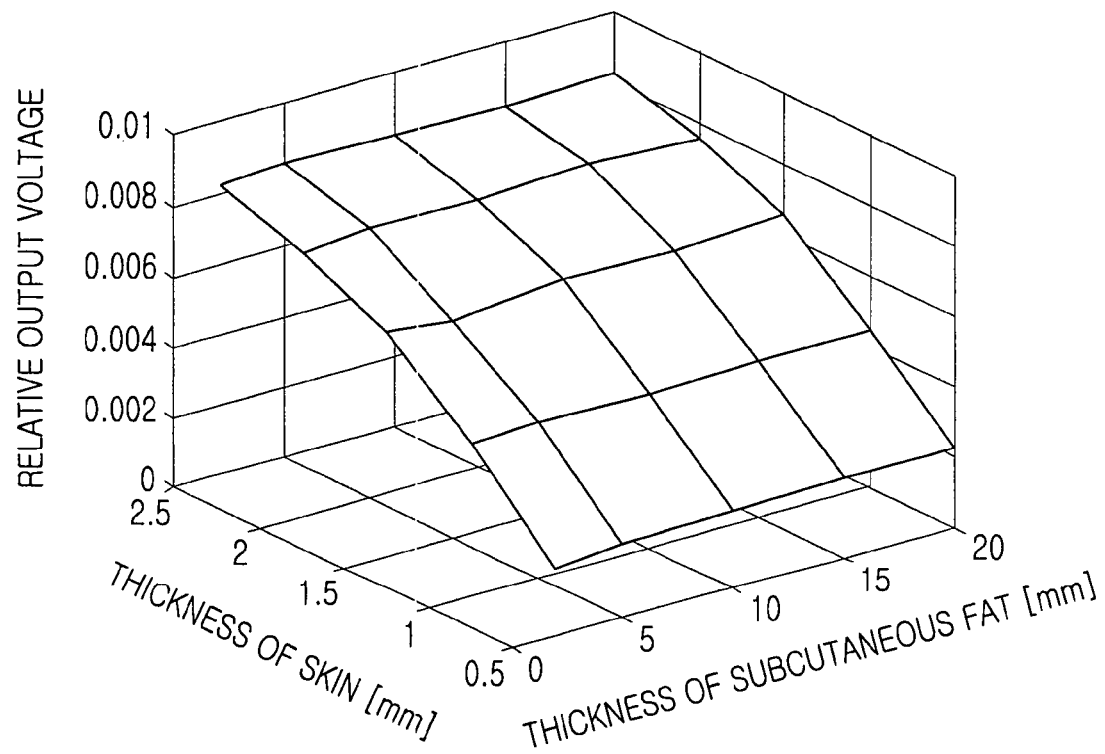
FIGS. 5 and 6 are views showing the relationship between the thickness of skin and the intensity of a first detection light in people with white skin and people with black skin, respectively.
Figure 6:
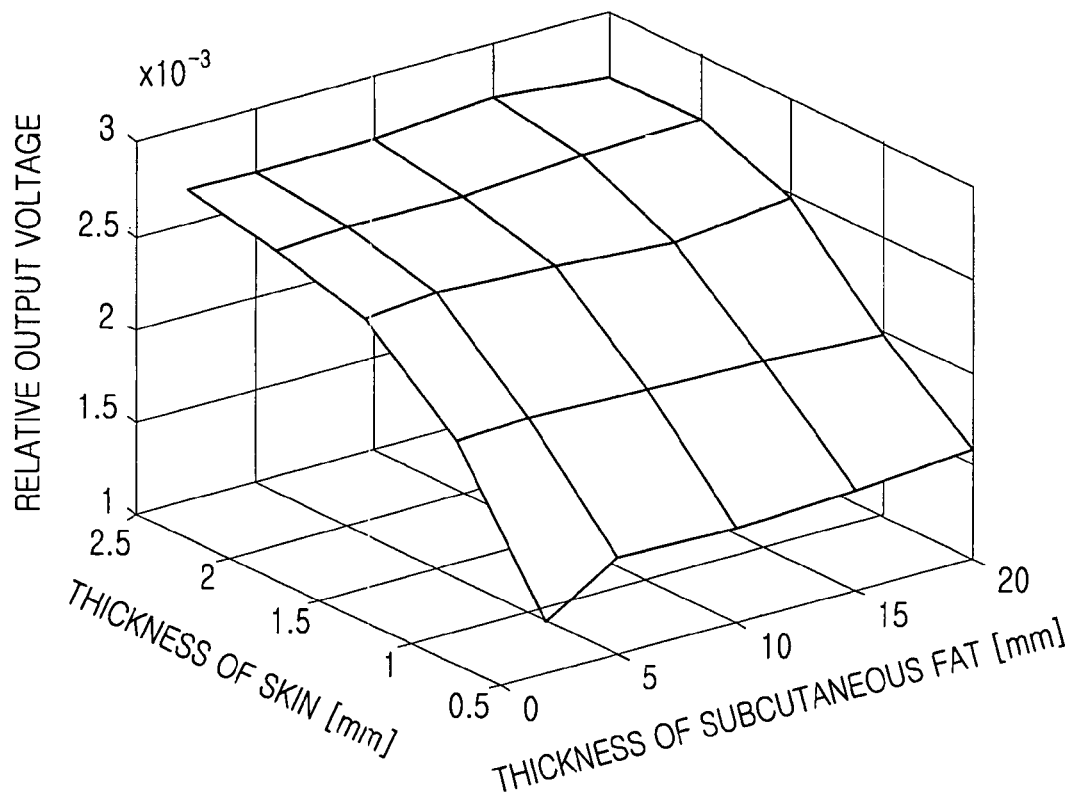

FIGS. 5 and 6 are views showing the relationship between the thickness of skin 276 and the intensity of a first detection light in a visible light wavelength range (for example, 660 nm) in the skin with low melanin index and the skin with high melanin index, respectively. In FIGS. 5 and 6, the intensity of a first detection light is indicated by a relative output voltage, which represents a ratio of a reference voltage to an output voltage of the optical detector 210. FIG. 5 is a three-dimensional view showing the relationship between the thickness of skin 276 and the intensity of the first detection light, and the relationship between the thickness of subcutaneous fat 274 and the intensity of the first detection light in the skin with low melanin index. FIG. 6 is a three-dimensional view showing the relationship between the thickness of skin 276 and the intensity of the first detection light, and the relationship between the thickness of subcutaneous fat 274 and the intensity of the first detection light in skin with high melanin index.

Referring to FIGS. 5 and 6, in both of the skins with low and high melanin indices, the intensity of the first detection light increases slightly with increase in the thickness of the subcutaneous fat 274, whereas the intensity of the first detection light increases significantly with increase in the thickness of the skin 276. Although, variations in the intensity of the first detection light according to the variations in the thickness of the subcutaneous fat 274 are similar in both skins, the skin with low melanin index shows greater variations in the intensity of the first detection light according to the variations in the thickness of the skin 276.

Figure 7:
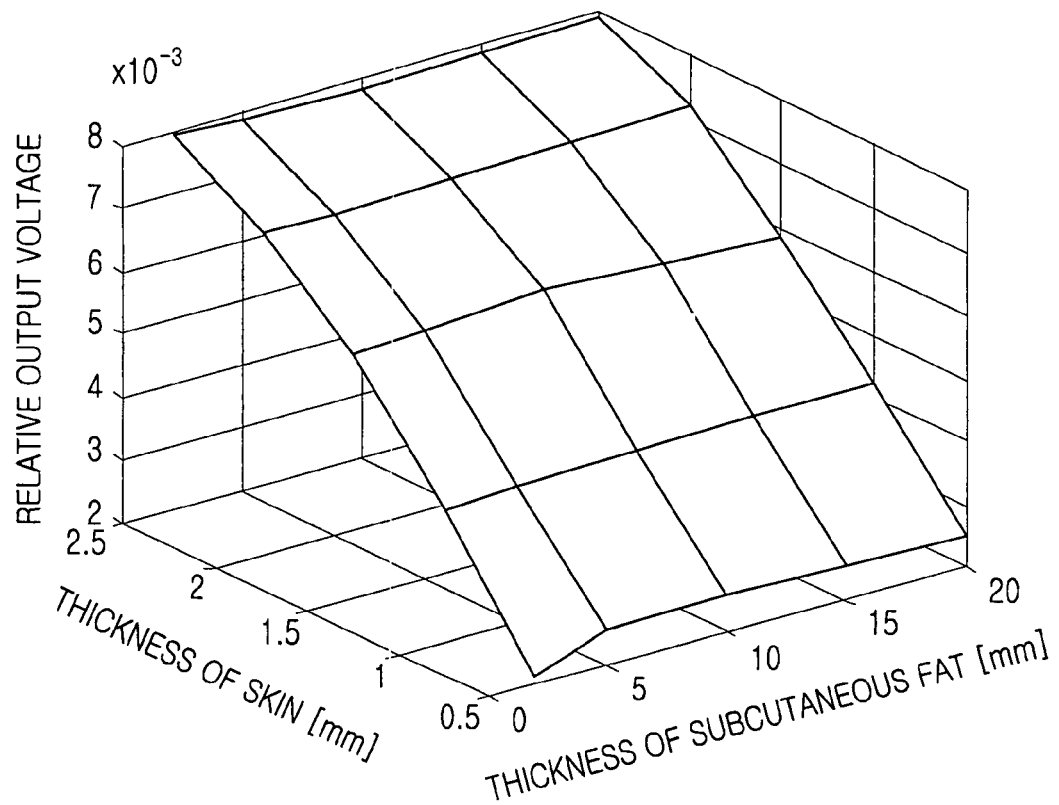
FIGS. 7 and 8 are views showing the relationship between the thickness of skin and the intensity of a second detection light in people with white skin and people with black skin, respectively.
Figure 8:
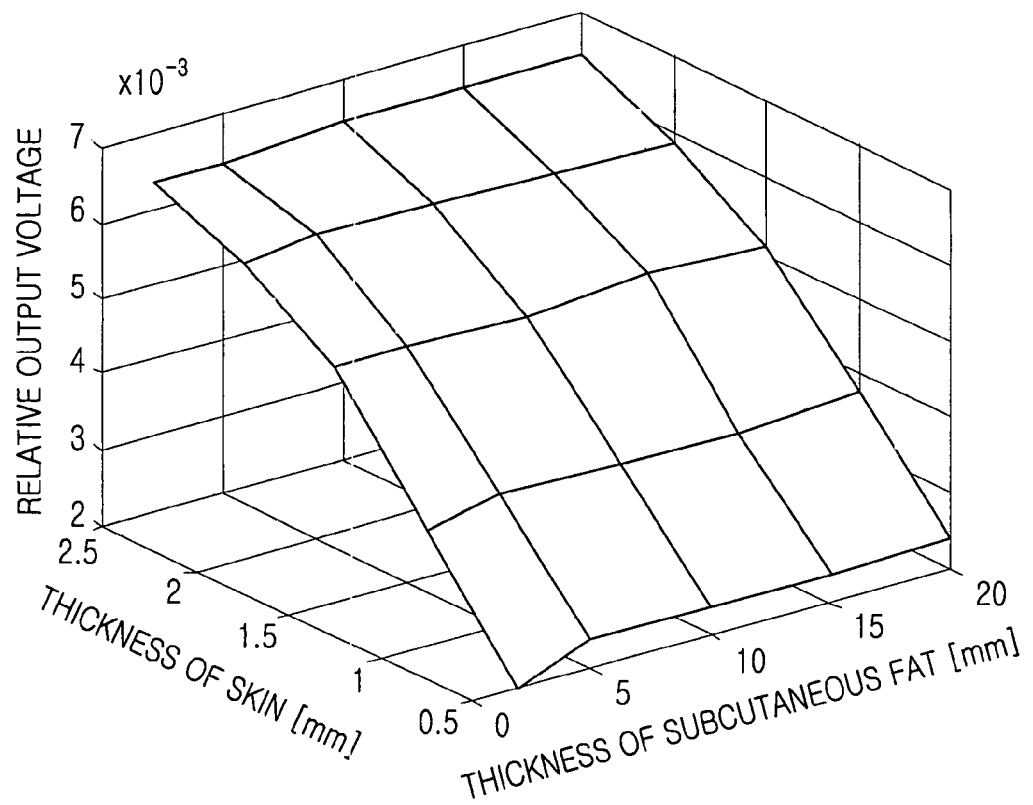

FIGS. 7 and 8 are views showing the relationship between the thickness of skin 276 and the intensity of a second detection light in a near-infrared wavelength range (for example, 940 nm) in the skin of low melanin index and in the skin with high melanin index, respectively. FIG. 7 is a three-dimensional view showing the relationship between the thickness of skin 276 and the intensity of the second detection light, and the relationship between the thickness of subcutaneous fat 274 and the intensity of the second detection light in the skin with low melanin index. FIG. 8 is a three-dimensional view showing the relationship between the thickness of skin 276 and the intensity of the second detection light, and the relationship between the thickness of subcutaneous fat 274 and the intensity of the second detection light in the skin with high melanin index.

In both skins, the intensity of the second detection light increases slightly with increase of the thickness of the subcutaneous fat 274, whereas the intensity of the second detection light increases significantly with increase of the thickness of the skin 276. Variations in the intensity of the second detection light according to the variations in the thickness of the subcutaneous fat 274 or the skin 276 are similar in both skins.

As shown in FIGS. 5 to 8, the intensity of the first detection light having a wavelength in visible light bandwidth varies greatly according to the thickness and color of the skin 276. Although variations in the intensity of the second detection light having a near-infrared wavelength are not as significant in skins of different colors, the intensity of the second detection light varies significantly according to the thickness of the skin 276.

Figure 9:
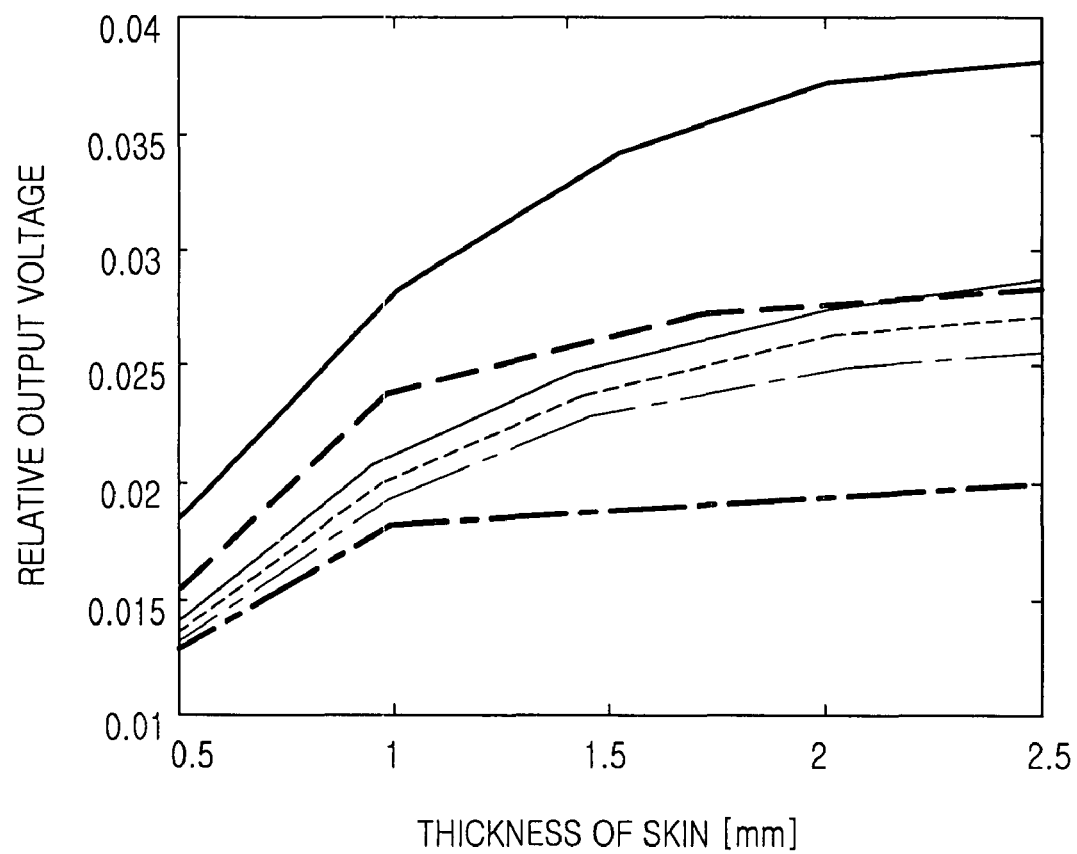
FIG. 9 is a graph showing the relationship between the thickness and color of skin and the intensities of first and second detection lights.

FIG. 9 is a graph showing the relationship between the thickness of skins, the color of skins, and the intensities of first and second detection lights. In FIG. 9, variations in the intensity of the first detection light according to the thickness of skin are represented by bold lines, while variations in the intensity of the second detection light are represented by thin lines. In addition, solid lines are applicable to the skin with low melanin index, the "white" skin; the dotted lines are applicable to the skin with intermediate melanin index, the "yellow" skin; and one-dot chain lines are applicable to the skin with high melanin index, the "darker" skin.

As shown in the graph of FIG. 9, the intensity of the first detection light increases with an increase of the thickness of the skin 276 in all three skins. In addition, variations in the intensity of the first detection light according to different colors of skin are greater than the variations in the intensity of the second detection light.

Further, greater the melanin index of the skin or darker the skin color, greater the absorption index or the absorption rate. Moreover, the intensities of the first and second detection lights decrease with an increase of the absorption index. Such results are clearly detectable in the visible light bandwidth, but not as detectable in the near-infrared bandwidth, as melanin has higher absorption index or rate in the visible light bandwidth.

Referring back to FIGS. 3 and 4, the controller 250 of the first aspect of the present invention sequentially drives the first light sources 220, the second light sources 230, and the third light source 240. In addition, the controller 250 determines the thickness and color of the skin 276, and the thickness of the subcutaneous fat 274 based on the intensities of the first to third detection lights sequentially detected by the optical detector 210. To achieve such determinations, the controller 250 is electrically connected to the optical detector 210, the first light sources 220, the second light sources 230, and the third light source 240; receives an output signal from the optical detector 210; and outputs a driving signal to the first light sources 220, the second light sources 230, and the third light source 240.

Although it is described that the controller 250 sequentially drives the first light sources 220, the second light sources 230, and the third light source 240, a person of ordinary skill in the art will appreciate that the driving order may be changed.

Figure 10:
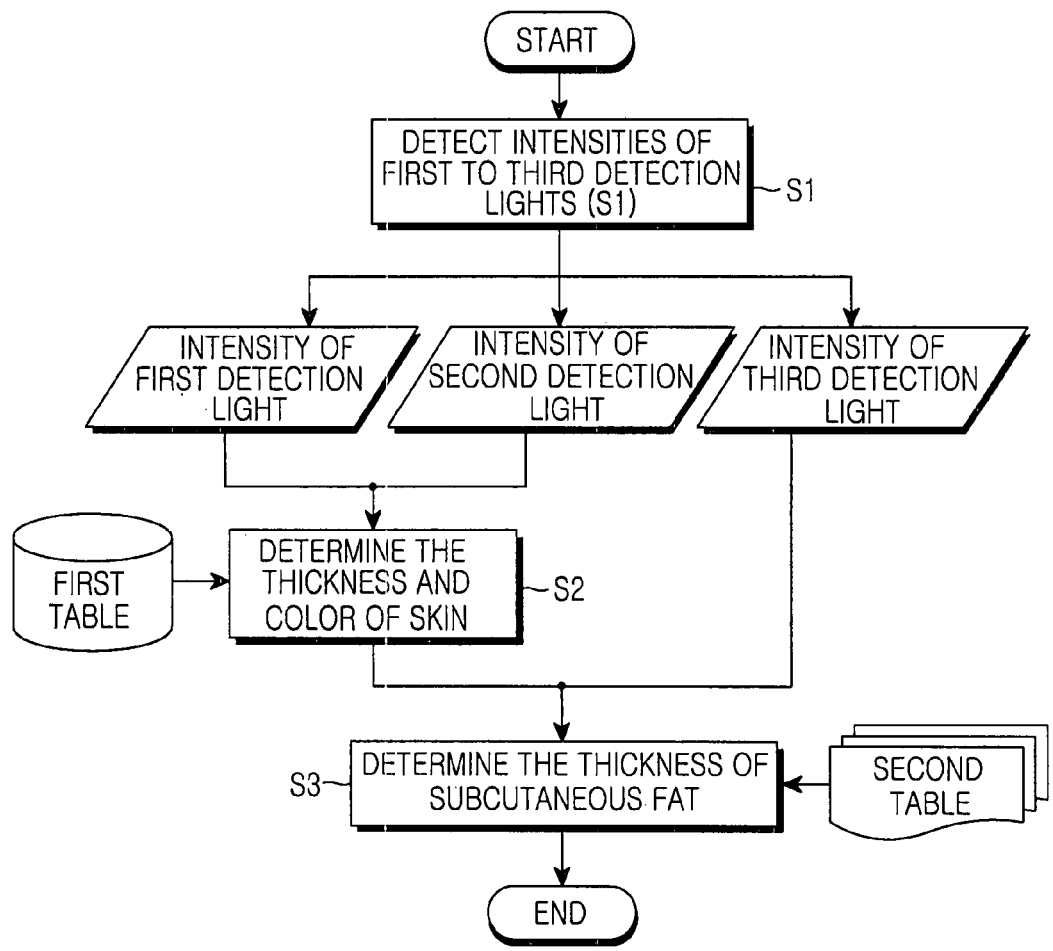
FIG. 10 is a flowchart showing the control process performed by the controller in FIG. 4.

FIG. 10 is a flowchart showing the control process performed by the controller 250. The control process includes processes S1 to S3, as explained below.

Process S1 is performed to detect the intensities of first to third detection lights. The controller 250 sequentially drives the first light sources 220, second light sources 230 and third light source 240, and the controller 250 detects the intensities of the first to third detection lights which are sequentially detected by the optical detector 210. An electric signal outputted from the optical detector 210 has a voltage level corresponding to the intensity of light inputted to the optical detector 210. The controller 250 may be a digital element without an analogue/digital interface. In the alternative, each of the optical detector 210, the first light sources 220, the second light sources 230, and the third light source 240 may be an analogue element without analogue/digital interface. In the latter case, an analogue-to-digital converter may be provided between the controller 250 and the optical detector 210, and digital-to-analogue converters may be provided between the controller 250 and each of the first, second and third light sources 220, 230 and 240.

In process S2, the thickness and color of the skin 276 is analyzed based on the intensities of the first to third detection lights and the first table. In other words, process S2 maps the intensities of the first to third detection lights according to the thickness and color of the skin 276. The first table has discrete, discontinuous data sets, the data sets comprising {intensity of first detection light, intensity of second detection light}—{skin color, skin thickness}. Accordingly, the thickness and color of the skin 276 may be determined based on the intensities of the first and second detection lights. However, due to discontinuity of the data sets, the mapping process using an approximation algorithm is required.

The mapping process is divided into a first process of mapping the color of the skin 276 to the intensities of the first and second detection lights, and a second process of mapping the thickness of the skin 276 to the intensities of the first and second detection lights. Various algorithms are known for estimating an unknown parameter with two given parameters in discrete data sets having three parameters. Given the intensities of the first and second detection lights, the thickness and the color sought may be conformed to the known values or an intermediate value thereof using an approximation algorithm.

The memory 260 further stores a second table showing the relationship between the thickness of the subcutaneous fat 274 and the intensity of the third detection light according to the thickness and color of skin 276. After the thickness and color of the skin 276 is determined, the thickness of the subcutaneous fat 274, which corresponds to the intensity of the third detection light, may be determined using the second table. As the first and second tables stored in the memory 260 include the thickness and the color of the skin 276 as common parameters, it is advantageous to conform the thickness and color sought to the known values to expedite the process.

Figure 11:
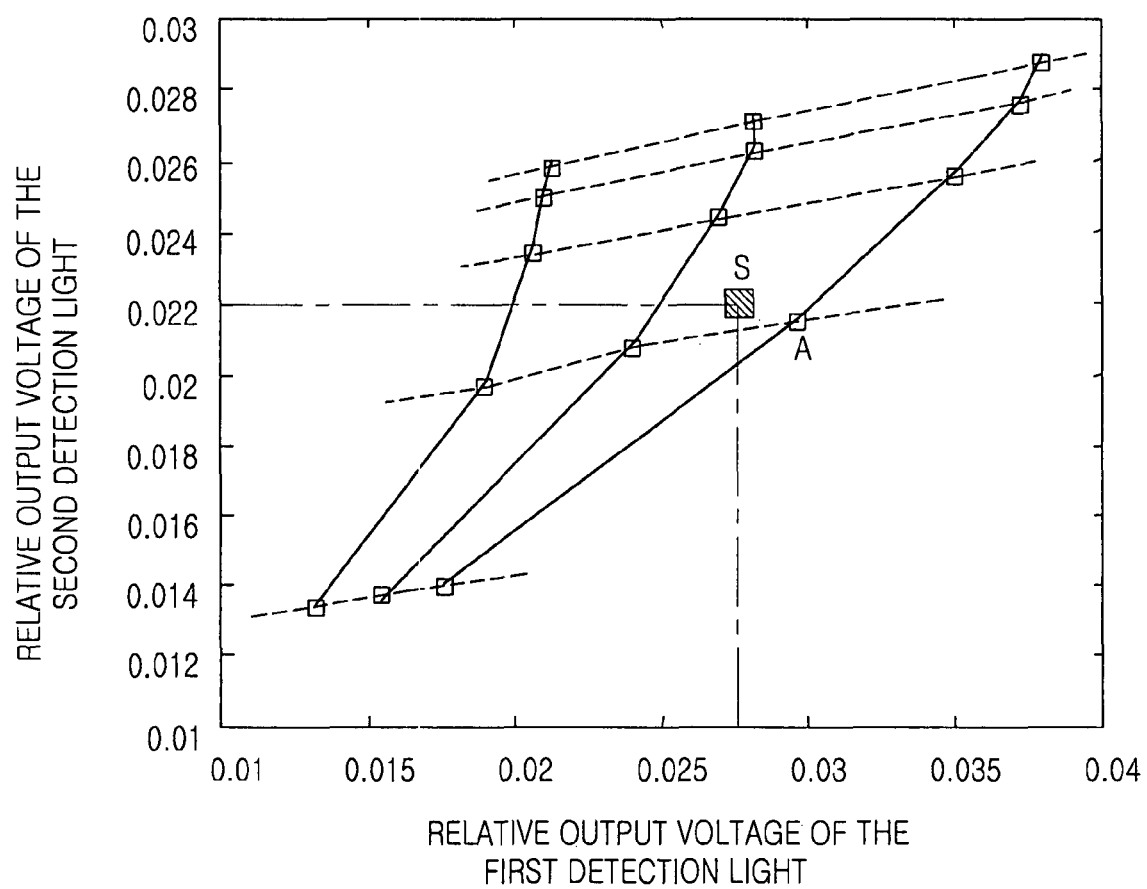
FIG. 11 is a graph for explaining a process of mapping the intensities of first and second detection lights to the skin thickness and color.

FIG. 11 is a graph for explaining a process of mapping the intensities of first and second detection lights to the skin thickness and color. The transverse axis represents the intensity of the first detection light, whereas the longitudinal axis represents the intensity of the second detection light. The empty squares represent data sets stored in the first table. The solid lines are the skin color lines or curves drawn through points representing data sets of the same skin color. The dotted lines are skin thickness lines or curves drawn through points representing data sets of the same skin thickness. In the graph, five thickness lines, from the bottom to top, correspond respectively to 0.5, 1.0, 1.5, 2.0 and 2.5 mm thickness of skin. Three skin color lines, from left to right, correspond respectively to the skin with high, intermediate, and low melanin indices. When the first and second detection lights have intensities of 0.0275 and 0.022 ("data set S"), the mapping process will be performed as follows.

At a first stage, data set S is compared repeatedly with another data set using an algorithm for obtaining a distance between two points to find data set A, which is the most approximate to data set S.

At a second stage, when two or more data sets are found to be approximate of the data set S, a data set closest to the standard thickness and the standard color of the skin is selected.

At a third stage, {skin color, skin thickness} of data set S is set to be identical to {skin color, skin thickness} of data set A.

In the process S3 the thickness of the subcutaneous fat 274 is analyzed based on the intensity of the third detection light and the second table. As in process S2, the process S3 maps the intensity of the third detection light to the thickness of the subcutaneous fat 274. The second table has discrete, discontinuous data sets, the data sets comprising {skin color, skin thickness}—{intensity of third detection light, thickness of subcutaneous fat}. Accordingly, the thickness of the subcutaneous fat 274 may be determined based on the thickness and color of the skin 276 and the intensity of the third detection light. However, due to the discontinuity of the data sets, a mapping process using an approximation algorithm is required. Various algorithms are known for estimating an unknown parameter with one given parameter in discrete data sets having two parameters. Given the thickness and color of the skin 276 and the intensity of the third detection light, the thickness of the subcutaneous fat 274 may be conformed to the known values or an intermediate value thereof using an approximation algorithm.

Figure 12:
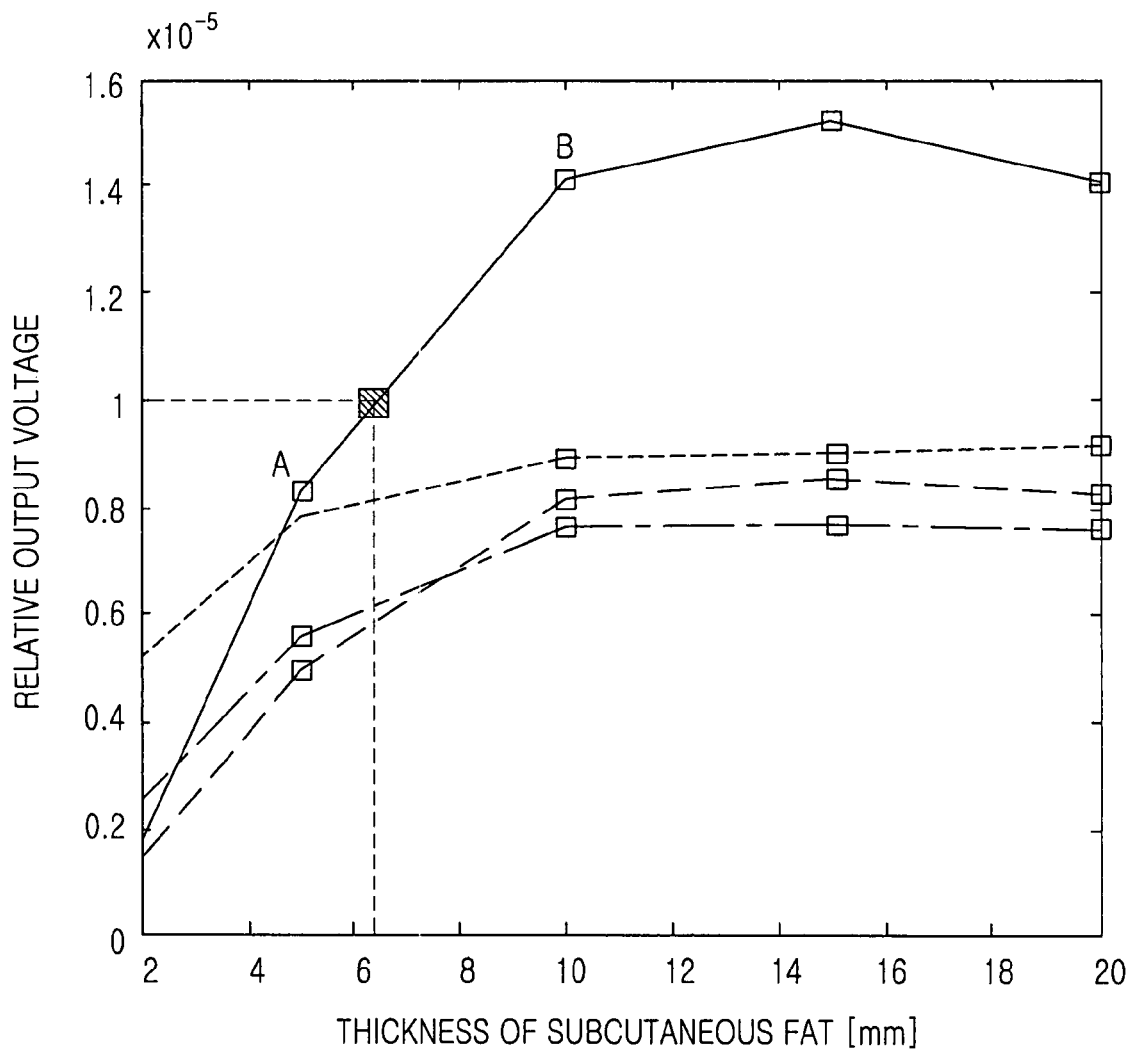
FIG. 12 is a graph for explaining a process of mapping the intensity of a third detection light to the subcutaneous fat thickness.

FIG. 12 is a graph for explaining a process of mapping the intensity of a third detection light to the subcutaneous fat thickness. In this graph, the longitudinal axis represents the intensity of the third detection light, while the transverse axis represents the thickness of the subcutaneous fat 274. For purposes of explaining the present invention, convenience, and brevity, only the data sets concerning skin with low melanin index will be referred to in connection with FIG. 12.

As shown in FIG. 12, the empty squares in the graph represents data sets stored in the second table. The solid line connects points representing data sets of 0.5 mm skin thickness. The long-dash-dotted line connects points representing data sets of 1.0 mm skin thickness. The one-dot chain line connects points representing data sets of 1.5 mm skin thickness. The short-dash-dotted line connects points representing data sets of 2.0 mm skin thickness. FIG. 12 clearly shows that when the thickness of the subcutaneous fat 274 is 2 mm, the intensity of the third detection light is highest at the skin thickness of 2.0 mm, and becomes lower at 1.5, 0.5 and 1.0 mm. When the thickness of the subcutaneous fat 247 is 6 mm, the intensity of the third detection light is the highest at the skin thickness of 0.5 mm, and becomes lower at 2.0, 1.5 and 1.0 mm.

When the intensity of the third detection light is 1.0 in the skin with low melanin index having a skin thickness of 0.5 mm ("data set S"), the mapping process will be performed as follows.

At a first stage, data set S is compared repeatedly with another data set in order to find two data sets A and B which have data set S therebetween.

At a second stage, an equation of a straight line connecting data sets A and B is obtained.

At a third stage, the intensity "1.0" of the third detection light is substituted into the equation to obtain the thickness of the subcutaneous fat 274.

At a subsequent stage, a process of visually displaying the thickness and color of the skin 276 and the thickness of the subcutaneous fat 274 may be further performed by the controller 250. In order to perform such subsequent process, the living body measurement apparatus 200 may further include a display unit, such as an LCD (Liquid Crystal Display), which is electrically connected to the controller 250.

The living body measurement apparatus 200 according to the present invention is applicable to mobile terminals, such as cellular phones and PDAs (Personal Digital Assistants), or wearable devices. The living body measurement apparatus 200 can be integrated into a mobile terminal or modularized to be mountable onto a mobile terminal. The living body measurement apparatus 200 may include at least one optical detector 210, at least one first light source 220, at least one second light source 230, at least one third light source 240 and a controller 250. The apparatus 200 may transmit an output from the optical detector 210 to a mobile terminal through a cable. Alternatively, the apparatus 200 may transmit the output from the optical detector 210 wirelessly to the mobile terminal using an antenna. In the latter case, the living body measurement apparatus 200 may only implement the function of sequentially driving the first light source 220, second light source 230 and third light source 240. The mapping process explained above can be performed by a controller of the mobile terminal, rather than by the living body measurement apparatus 200.

In consideration of the directional characteristic of living body tissues, it may be necessary to increase the number of the optical detector 210 and the third light source 240, as well as the first and second light sources 220 and 230.

In such a case, however, the manufacturing cost of the living body measurement apparatus 200 will increase. The following aspects of the present invention provide structures which may minimize the number of light sources using a waveguide and which can compensate any errors attributable to the directional characteristic of a living body tissue.

Figure 13:
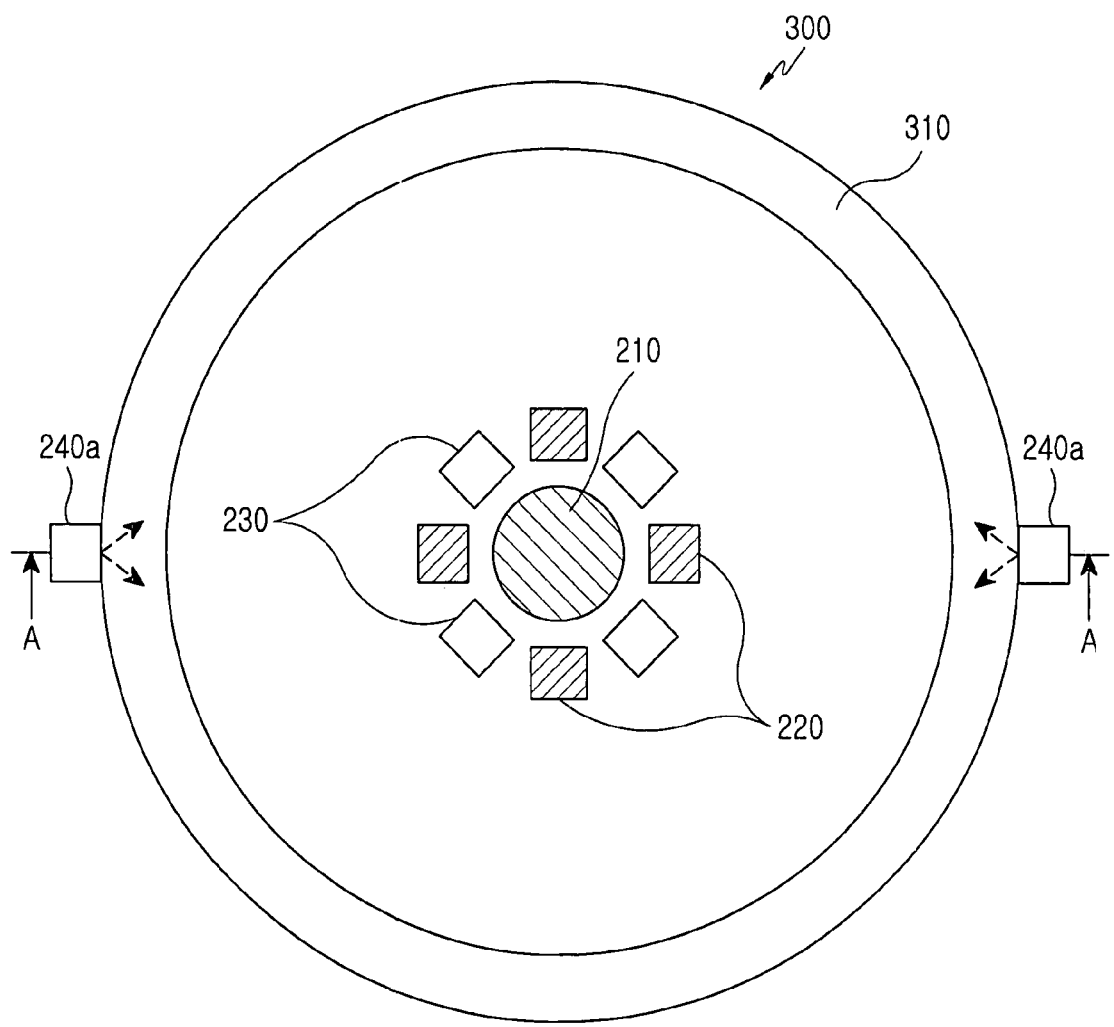
FIG. 13 illustrates a living body measurement apparatus according to a second aspect of the present invention.
Figure 14:
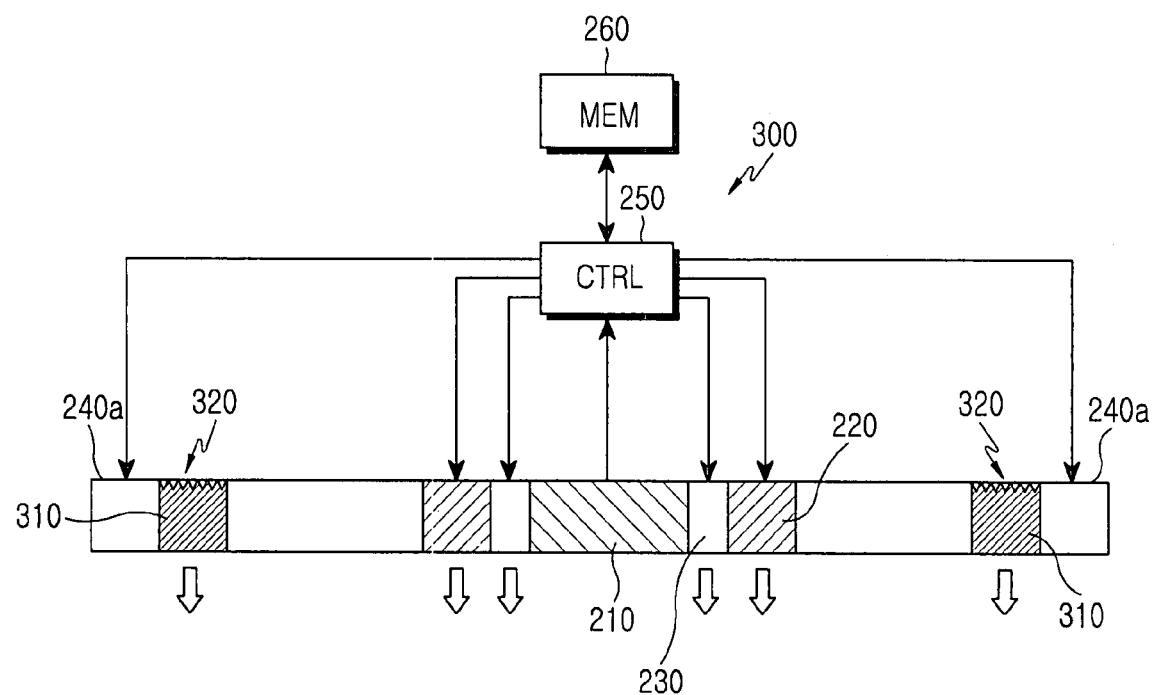
FIG. 14 is a cross-sectional view of the living body measurement apparatus in FIG. 13.

FIG. 13 illustrates a living body measurement apparatus 300 according to a second aspect of the present invention. FIG. 14 is a cross-sectional view taken along the line A-A in FIG. 13. A living body measurement apparatus 300 according to the second embodiment of the present invention has a configuration and functions which are similar to those of the apparatus 200 illustrated in FIG. 3. The apparatus 300 differs from the apparatus 200 only in that it has a plurality of third light sources 240a and further includes a waveguide 310. Accordingly, the same features as included in the apparatus 200 will be designated by the same drawing reference numerals as used in relation to the apparatus 200, and any repetitive explanation of the features, including the explanation of the distances between the components that may function as the output terminals and the components that may function as the input terminal of the detector, will be omitted.

The living body measurement apparatus 300 includes an optical detector 210, a plurality of first light sources 220, a plurality of second light sources 230, a plurality of third light sources 240a, a waveguide 310, a controller 250 and a memory 260. The controller 250 and the memory 260 are not depicted in FIG. 13.

The optical detector 210 is placed on the surface of the skin (not shown) and outputs an electric signal obtained by photoelectric conversion of the inputted light. In other words, the optical detector 210 detects the light penetrating up through the skin 276 and inputted to the optical detector 210 as an electric signal, after converting the inputted light to an electrical signal. The bottom of the optical detector 210, which functions as an input terminal, may be in a direct contact with the surface of the skin 276, or, alternatively, be separated from the surface of the skin 276.

As shown in FIG. 13, four of the first light sources 220 and four of the second light sources 230 may be disposed at an equal distance from and along the outer perimeter of the optical detector 210. These light sources 220 and 230 are reciprocally disposed and equally spaced from adjacent light sources.

The first light sources 220 are disposed on the surface of the skin 276 at a predetermined distance from the optical detector 210. The first light sources 220 radiate a first light having a first wavelength, for example, 660 nm, in a visible light bandwidth onto the surface of the skin 276. The bottom of each first light source 220, which functions as an output terminal, may be in a direct contact with the surface of the skin 276, or, alternatively, separated from the surface of the skin 276.

The second light sources 230 are disposed on the surface of the skin 276 at a predetermined distance from the optical detector 210. The second light sources 230 radiate a second light having a second wavelength, for example, 940 nm, in a near-infrared bandwidth onto the surface of the skin 276. The bottom of each second light source 230, which functions as an output terminal, may be in a direct contact with the surface of the skin 276, or, alternatively, separated from the surface of the skin 276.

The waveguide 310 having a ring shape is disposed on the surface of the skin and surrounds the first and second light sources 220 and 230. The waveguide 310 has inner and outer peripheries, and top and bottom surfaces. The bottom surface of the waveguide 310, which functions as an output terminal, may be in a direct contact with the surface of the skin 276, or, alternatively, separated from the surface of the skin 276. The cross-section perpendicular to the circumference (i.e., to the direction of the diameter) of the waveguide 310 is in a shape of a quadrilateral. The waveguide 310 has a refractive index that is higher than those of the air and the skin, and light traveling within the waveguide 310 travels in circumferential direction, via total internal reflection. The waveguide 310 may be formed by injection molding, and the waveguide 310 may be made of polycarbonate or acryl-based resin that exhibits transparency over the wavelength of the third light. The waveguide 310 may comprise other materials including a rubber material having transparency over the wavelength of the third light, preferably polyurethane or silicone.

A plurality of light extracting patterns 320 may be provided on the top surface of the waveguide 310 in order to output light traveling in the waveguide 310 through the bottom surface. The light extracting patterns 320 scatter incident light. These patterns 320 are formed symmetrically with respect to the center of the waveguide 310. Each light extracting pattern 320 destroys the conditions for total internal reflection of light incident upon the interface of the waveguide 310 and the air or the interface of the waveguide 310 and the skin, so that the light scattered by the pattern 320 can penetrate through the bottom surface of the waveguide 310. In particular, a portion of the light scattered toward the bottom of the waveguide 310 by the light extracting pattern 320 does not meet the total reflection conditions, as the angle of light incident upon the bottom surface is less than the critical angle. Such portion of the light penetrates the bottom surface of the waveguide 310 and exits the waveguide 310.

Meanwhile, a portion of the light that is not scattered, and the portion of the scattered light which meets the total reflection conditions, travels through the waveguide 310 and be incident on another, second light extracting pattern 320. A portion of the light that is incident upon the second light extracting pattern 320 is scattered by the second light extracting pattern 320, penetrates the bottom surface of the waveguide 310, and exits the waveguide 310.

The light extracting patterns 320 may be scratches, convexo-concavo, or prism patterns formed by a process including printing, photolithography, lasing, or stamping. Each of the light extracting patterns 320 may be of variety of shapes, such as a circular cone, dome, hexahedron, triangular pyramid or square pyramid. In addition, the light extracting patterns 320 may also be carved in the form of relief or intaglio on the bottom surface of the waveguide 310.

In forming the waveguide 310 and the light extracting patterns 320, desired patterns 320 may be applied to a mold in order to simultaneously form the waveguide 310 and the light extracting patterns by injection molding. In addition, each light extracting pattern 320 can be a Bragg grating having a periodic variation in refractive index. The refractive index variation is induced by polling or ultraviolet radiation.

Although the above description may appear to limit the light extracting patterns 320 in the second aspect of the present invention to those scattering the incident light, such is not the case. The patterns may also be formed in a V-groove shape which causes specular reflection, or the patterns may be formed in a coating layer which has a refractive index similar to that of the waveguide 310.

Moreover, it has been explained that a plurality of light extracting patterns 320 are formed on the top surface within the waveguide 310. However, a single light extracting pattern 320 may be formed over the entire top surface within the waveguide 310.

The third light sources 240a are disposed symmetrically with respect to the optical detector 210. An output terminal of each third light source 240a faces the outer peripheral surface of the waveguide 310. The third light sources 240a couple the third light having a second wavelength in near-infrared bandwidth into the waveguide 310.

The light from the third light sources 240a and coupled into the waveguide 310 attenuates gradually as it travels through the waveguide 310 in the circumferential direction by total internal reflection. Within the waveguide 310, the intensity of the light relatively closer to the third light sources 240a may be greater than the intensity of the portion of the light relatively farther away from the third light sources 240a. The discrepancy in the intensity may be remedied by varying the density or size of the light extracting patterns 320. For example, the light extracting patterns 320 relatively closer to the third light sources 240a may have a lower density than those relatively farther away from the third light sources 240a such that the overall light within the waveguide 310, regardless of the distance from the third light sources 240a, may be uniformly distributed within the waveguide 310.

Figure 15:
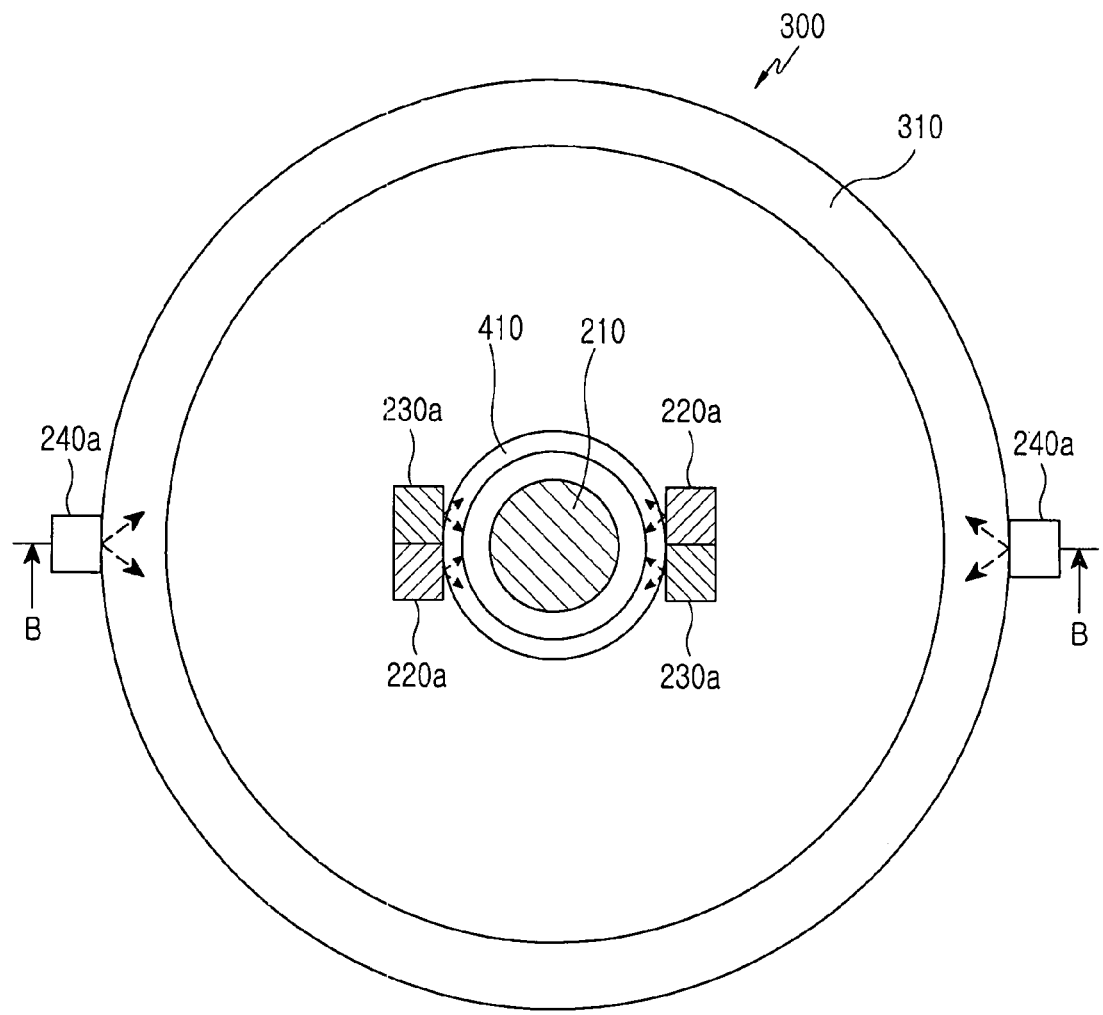
FIG. 15 illustrates a living body measurement apparatus according to a third aspect of the present invention.
Figure 16:
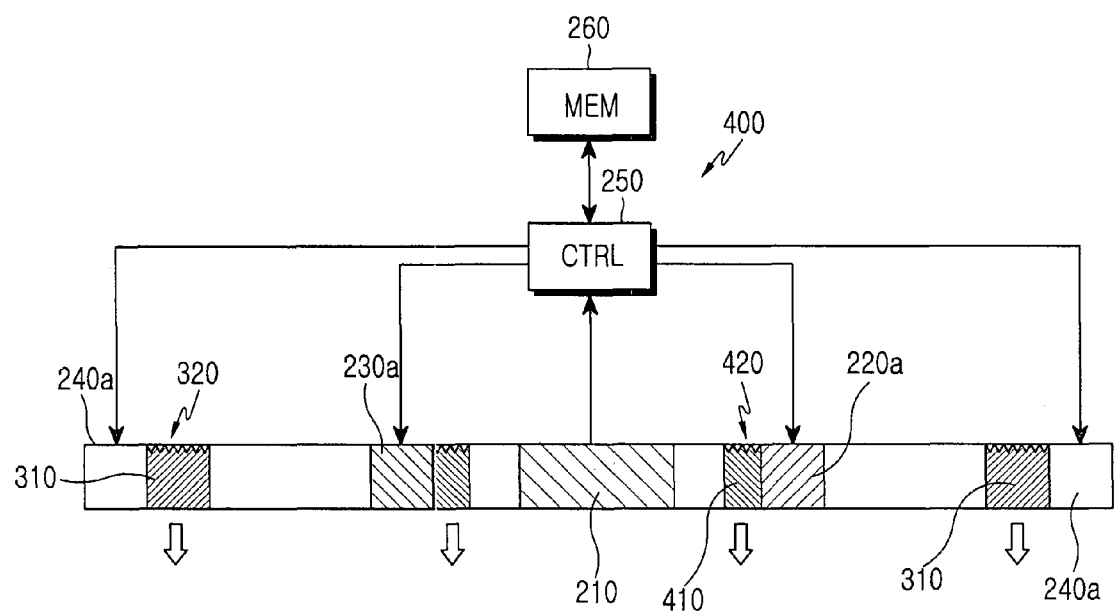
FIG. 16 is a cross-sectional view of the living body measurement apparatus in FIG. 15.

FIG. 15 illustrates a living body measurement apparatus according to a third aspect of the present invention. FIG. 16 is a cross-sectional view taken along the line A-A in FIG. 15. A living body measurement apparatus 400 according to the third embodiment of the present invention has a configuration and functions similar to those of the apparatus 300 illustrated in FIG. 13. The apparatus 400 differs from the apparatus 300 only in the number and disposition of first and second light sources 220a and 230a and in further inclusion of a second waveguide 410. Accordingly, the same features as included in the apparatus 300 will be designated by the same drawing reference numerals as used in relation to the apparatus 300, and any repetitive explanation of the features, including the explanation of the distances between the components that may function as the output terminals and the components that may function as the input terminal of the detector, are omitted.

The living body measurement apparatus 400 includes an optical detector 210, a plurality of first light sources 220a, a plurality of second light sources 230a, a plurality of third light sources 240a, a first waveguide 310, a second waveguide 410, a controller 250 and a memory 260.

The second waveguide 410 having a circular ring shape is disposed on the surface of the skin (not shown) and surrounds the optical detector 210. The second waveguide 410 has inner and outer peripheries, as well as top and bottom surfaces. The bottom surface of the second waveguide 410, which functions as an output terminal, may be in a direct contact with the surface of the skin, or, alternatively, separated from the skin. The cross-section perpendicular to the circumference (i.e., to the direction of the diameter) of the second waveguide 410 has a shape of a quadrilateral. The second waveguide 410 has a refractive index that is higher than those of the air and the skin, and the light traveling within the second waveguide 410 travels in the circumferential direction via total internal reflection. The second waveguide 410 may made from the same material as the first waveguide 310.

A plurality of light extracting patterns 420 may be provided on the top surface of the second waveguide 410 in order to output light traveling in the second waveguide 410 through the bottom surface. The light extracting patterns 420 scatter incident light. These patterns 420 are formed symmetrically with respect to the center of the second waveguide 410. Each light extracting pattern 420 destroys the conditions for internal total reflection of the light upon the interface of the second waveguide 410 and the air or the interface of the second waveguide 410 and the skin so that the light scattered by the pattern 420 can penetrate through the bottom surface of the second waveguide 410. In particular, a portion of the light scattered toward the bottom of the second waveguide 410 by the light extracting pattern 420 does not meet the total reflection conditions, as the angle of light incident upon the bottom surface is less than the critical angle. This portion of the light penetrates the bottom surface of the second waveguide 410 and exits the second waveguide 410.

Meanwhile, a portion of the light that is not scattered and the remaining scattered light which meets the total reflection conditions, travels through the second waveguide 410 and be incident on another, second light extracting pattern 420. A portion of the light that is incident upon the second light extracting pattern 420 is scattered by the second light extracting pattern 420, penetrates the bottom surface of the second waveguide 410, and exits the second waveguide 410.

The light extracting patterns 420 may be scratches, convexo-concavo or prism patterns formed by a process including printing, photolithography, lasing or stamping. In addition, the light extracting patterns 420 may have the same form, including the shape, the configuration, or the material, as the light extracting patterns 320 of the first waveguide 310.

The first light sources 220a are disposed symmetrically with respect to the optical detector 210. An output terminal of each first light source 220a faces the outer peripheral surface of the second waveguide 410. Similarly, the second light sources 230a are disposed symmetrically with respect to the optical detector 210, and their output terminals faces the outer peripheral surface of the second waveguide 410. Each of the first light sources 220a outputs and couples a first light having a first wavelength into the second waveguide 410. Meanwhile, each of the second light sources 230a outputs and couples a second light having a second wavelength into the second waveguide 410. Although FIGS. 15 and 16 illustrate that the third aspect of the present invention provides a pair of the first light source 220a and the second light source 230a contacting one another at both sides of the second waveguide 410, it is also possible to dispose the plurality of first light sources 220a at one side of the optical detector 210 and the plurality of second light sources 230a at the other side of the optical detector 210.

In relation to the above disclosure of the third aspect of the present invention, it has been explained that a living body measurement apparatus has one optical detector at the center thereof and a plurality of light sources disposed around the optical detector. However, the living body measurement apparatus may also have a configuration disposing a pair of light sources at the center of the apparatus and a plurality of optical detectors around the light sources.

Figure 17:
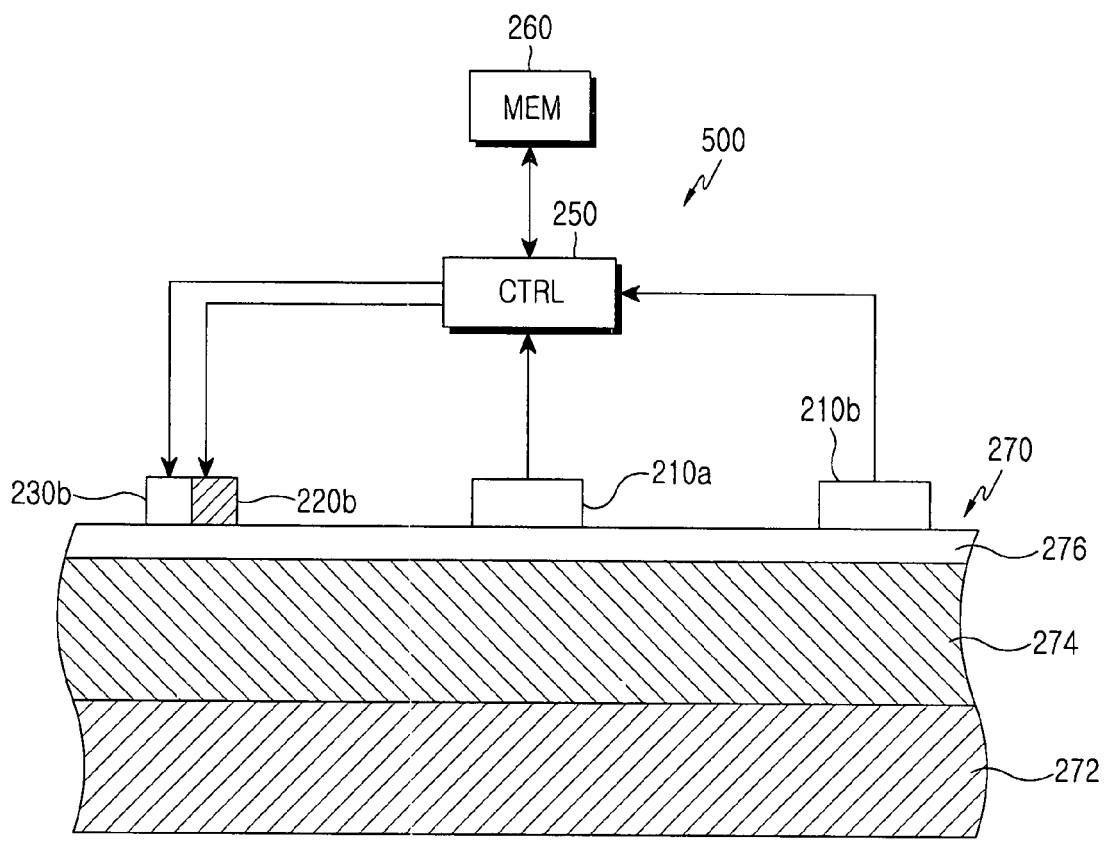
FIG. 17 illustrates a living body measurement apparatus according to a fourth aspect of the present invention.

FIG. 17 illustrates a living body measurement apparatus 500 according to a fourth aspect of the present invention. A living body measurement apparatus 500 according to the fourth embodiment of the present invention has a configuration and functions similar to those of the apparatus 200 illustrated in FIG. 3. The apparatus 500 differs from the apparatus 200 only in the number and disposition of optical detectors 210a and 210b and in the number and disposition of first and second light sources 220b and 230b. Accordingly, the same elements as included in the apparatus 200 will be designated by the same drawing reference numerals as used in relation to the apparatus 200, and any repetitive explanation are omitted.

A living body tissue 270 has a structure made up of muscle 272, fat 274 and skin 276.

The living body measurement apparatus 500 includes a first light source 220b, a second light source 230b, first and second optical detectors 210a and 210b, a controller 250 and a memory 260.

The first light source 220b is disposed on the surface of the skin 276, and radiates a first light having a first wavelength, for example, 660 nm, in visible light bandwidth onto the surface of the skin 276.

The second light source 230b is disposed on the surface of the skin 276, and radiates a second light having a second wavelength, for example, 940 nm, in a near-infrared bandwidth onto the surface of the skin 276.

The first optical detector 210a is disposed on the surface of the skin 276 at a predetermined distance from the first and second light sources 220b and 230b. The first optical detector 210a outputs an electric signal obtained by photoelectric conversion of the inputted light. In other words, the first optical detector 210a detects the light emitted from the surface of the skin 276 as an electric signal, after converting the inputted light into an electrical signal.

The second optical detector 210b is disposed on the surface of the skin 276 at a greater distance from the first and second light sources 220b and 230b than the first optical detector 210a. The second optical detector 210b outputs an electric signal obtained by photoelectric conversion of the inputted light. In other words, the second optical detector 210b detects the light emitted from the surface of the skin 276 as an electric signal after converting the inputted light to an electrical signal.

In accordance with the fourth aspect of the present invention, the distance between the first optical detector 210a and the first and second light sources 220b and 230b is not greater than 5 mm, while the distance between the second optical detector 210b and the first and second light sources 220b and 230b is not less than 10 mm. Preferably, the distance between the first optical detector 210a and the first and second light sources 220b and 230b is 2 mm, and the distance between the second optical detector 210b and the first and second light sources 220b and 230b is 10 mm.

Hereinafter, light inputted to the first optical detector 210a among the rays of the first light radiated from the first light source 220b will be referred to as "first detection light." Light inputted to the first optical detector 210a among the rays of the second light radiated from the second light source 230b will be referred to as "second detection light." Also, light inputted to the second optical detector 210b among the rays of the second light radiated from the second light source 230b will be referred to as "third detection light."

The memory 260 stores a first table showing the relationship between the intensities of the first and second detection lights and the thickness of the skin 276 and the relationship between the intensities of the first and second detection lights and the color of the skin 276. The memory 260 also stores a second table showing the relationship between the thickness of the subcutaneous fat 274 and the intensity of the third detection light according to the thickness and color of the skin 276.

The controller 250 sequentially drives the first light source 220b and the second light source 230b, and determines the thickness of the skin 276, the color of the skin 276, and the thickness of the subcutaneous fat 274 based on the intensities of the first and second detection lights sequentially detected by the first optical detector 210a. In addition, the controller 250 determines the thickness of the subcutaneous fat 274 based on the intensity of the third detection light, which is detected by the second optical detector 210b. To this end, the controller 250 is electrically connected to the first and second light sources 220b and 230b and the first and second optical detectors 210a and 210b. The controller 250 receives an output signal from the first and second optical detectors 210a and 210b, and outputs a driving signal to the first and second light sources 220b and 230b.

As several aspects of the present invention have been described for illustrative purposes, those skilled in the art will appreciate that various modifications, additions and substitutions are possible, without departing from the scope and spirit of the invention.

For example, it has been explained that the first and second light sources output respective lights having different wavelengths according to the fourth embodiment of the present invention. However, it is also possible to use a single light source which can output lights having different wavelengths simultaneously, or which can change wavelengths.

Although only the measurement of the skin thickness and color and the subcutaneous fat thickness has been explained above, various other body compositions can also be measured using the first to third detection lights. For example, it is possible to measure heart rate variability (in other words, stress level) by measuring a pulse wave in a finger tip, which is filled with capillaries, using light in a near-infrared wavelength range. In addition, the living body measurement apparatus can measure blood oxygen saturation (SpO2), photoplethysmography (PPG), respiratory frequency and pulse using light having a near-infrared wavelength and light having a visible light wavelength.

The living body measurement apparatus according to the present invention, unlike a conventional apparatus, does not disregard the effect various skin conditions may have on the measurement of body compositions. The apparatus measures the thickness and color of the skin directly and determines the thickness of subcutaneous fat accurately.

The living body measurement apparatus according to the present invention uses one or more waveguides to reduce the number of light sources. Accordingly, the apparatus is suitable for mobile terminals pursuing economic efficiency.

Therefore, various modifications, additions and substitutions can be made to the present invention, without departing from the scope and spirit of the invention as disclosed in the accompanying claims, including the full scope of equivalents thereof.

What is claimed is:

1. A measurement apparatus for measuring a particular body composition of a living body that determines skin color and skin thickness to output a measurement of the particular body composition, said apparatus comprising:
   a first light source being arrangeable in use when substantially in contact with a first position of a skin surface of a living body and being configured to radiate a first light having a visible light wavelength range onto the skin surface;
   a second light source being arrangeable in use when substantially in contact with a second position of the skin surface and being configured to radiate a second light in a near-infrared wavelength range onto the skin surface;
   an optical detector being arrangeable in use when substantially in contact with the skin surface at a predetermined distance from the first and second light sources and being configured to detect the first and second lights being output from the skin and convert the detected first and second lights into electric signals; and
   a controller configured for sequentially driving the first and second light sources and for determining skin color and skin thickness to output the particular composition of the living body based on a comparison of intensity values of lights detected and output by the optical detector with predetermined values in storage for a particular determined skin color and skin thickness;
   a waveguide being arrangeable in use when substantially in contact with the skin, between the optical detector and the first and second light sources, the waveguide being configured to allow the first or second light inputted from one of the first and second light sources to travel around the optical detector with total reflection; and
   at least one light extracting pattern being configured to extract the first or second light traveling with total internal reflection from the waveguide by scattering or reflecting the first or second light and being configured to radiate the first or second light onto the surface of the skin.

2. The measurement apparatus according to claim 1, further comprising a memory being configured to store a first table that maps intensities of the detected first and second lights and according to a particular thickness and color of the skin for plurality of thicknesses and colors, and wherein said controller is configured to determine the particular thickness and the color of the skin corresponding to the mapped intensities of the detected first and second lights in the first table.

3. The living body measurement apparatus according to claim 2, further comprising a third light source being arrangeable in use when substantially in contact with a surface of the skin at third position located farther away from the optical detector than the first and second light sources and being configured to radiate a third light onto the surface of the skin, wherein said optical detector is configured to detect the third light being output from the skin and converting the detected third light output from the skin into an electric signal, and wherein said controller is configured to sequentially drive the first, second, and third light sources.

4. The measurement apparatus according to claim 3, wherein said memory is configured to store a second table mapping a thickness of subcutaneous fat and an intensity of the detected third light, according to the thickness and color of the skin, and wherein said controller is configured to determine the thickness of the subcutaneous fat corresponding to the intensity of the detected third light, based on a comparison with the second table.

5. The measurement apparatus according to claim 2, wherein said optical detector comprises a first optical detector, and further comprising a second optical detector being arrangeable in use when substantially in contact with a surface of the skin at a location further away from the first and second light sources than the first optical detector, the second optical detector being configured to detect a third light output from the skin and convert the detected third light into an electric signal for output to the controller.

6. The measurement apparatus according to claim 5, wherein said memory being configured to store a second table mapping the thickness of a subcutaneous fat and an intensity of the detected third light, according to the determined thickness and color of the skin, and wherein said controller is configured to determine the thickness of the subcutaneous fat corresponding to the intensity of the detected third light based values in the second table.

7. The measurement apparatus according to claim 1, wherein said first light has a wavelength of substantially 660 nm.

8. The measurement apparatus according to claim 1, wherein said second light has a wavelength of 940 nm.

9. A measurement apparatus comprising:
   a first light source being arrangeable in use when substantially in contact with a first position of a skin in a living body and being configured to radiate a first light having a first visible wavelength onto the surface of the skin;
   a second light source being arrangeable in use when substantially in contact with a second position of the skin and being configured to radiate a second light having a second wavelength of near-infrared light that is different from the first wavelength onto the surface of the skin;
   a third light source being arrangeable in use when substantially in contact with the skin at a location further away from an optical detector than the first and second light sources and being configured to radiate a third light onto the surface of the skin;

an optical detector configured to detect each of the first light, second light, and third light output from the skin; and convert said each of the detected first light, detected second light, and detected third light into electric signals;

a controller configured to sequentially drive the first, second and third light sources and determine skin color and skin thickness to output a particular composition of a living body based on a comparison of intensity values of lights detected and output by the optical detector with predetermined values in storage for a particular determined skin color and skin thickness;

a waveguide being arrangeable in use when substantially in contact with the skin between the first and second light sources and the third light source and being configured to allow the third light inputted from the third light source to travel around the optical detector with total internal reflection; and at least one light extracting pattern being configured to extract the third light traveling with total internal reflection from the waveguide by scattering or reflecting the third light and being configured to radiate the third light onto the surface of the skin.

10. The measurement apparatus according to claim 9, further comprising a memory configured to store a first table mapping intensities of the detected first and second lights and a thickness of the skin, and mapping intensities of the detected first and second lights and a color of the skin, and wherein said controller is configured for determining the thickness and color of the skin corresponding to the intensities of the detected first and second lights, based on the first table.

11. The measurement apparatus according to claim 10, wherein said memory is being configured to store a second table mapping a thickness of subcutaneous fat and an intensity of the detected third light, according to the thickness and color of the skin, and wherein said controller is being configured to determine the thickness of the subcutaneous fat corresponding to the intensity of the detected third light, based on the second table.

12. The measurement apparatus according to claim 9, wherein said waveguide has a circular ring shape, a bottom surface contacting the skin, and a top surface at the opposite side of the bottom surface, said light extracting pattern being formed on the top surface of the waveguide.

13. The measurement apparatus according to claim 1, wherein said waveguide has a circular ring shape, a bottom surface contacting the skin, and a top surface at the opposite side of the bottom surface, said at least light extracting pattern being formed on the top surface of the waveguide.

14. The measurement apparatus according to claim 1, wherein said first light source and said second light source are provided by a single source that outputs light with different wavelengths simultaneously or which outputs light wavelengths of different wavelengths sequentially.

15. The measurement apparatus according to claim 1, wherein said waveguide has an endless ring shape, a bottom surface contacting the skin, and a top surface at the opposite side of the bottom surface, said at least light extracting pattern being formed on the top surface or the bottom surface of the waveguide.

16. The measurement apparatus according to claim 9, wherein said waveguide has an endless ring shape, a bottom surface contacting the skin, and a top surface at the opposite side of the bottom surface, said at least light extracting pattern being formed on the top surface or the bottom surface of the waveguide.

* * * * *